US007715606B2

(12) United States Patent
Jeung et al.

(10) Patent No.: US 7,715,606 B2
(45) Date of Patent: May 11, 2010

(54) MARKER SYSTEM AND METHOD OF USING THE SAME

(75) Inventors: Andrew G. Jeung, Mountain View, CA (US); Hassan Mostafavi, Los Altos, CA (US); Alexander Sloutsky, Burlingame, CA (US); Sergey Povzner, Burlingame, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 851 days.

(21) Appl. No.: 11/582,227

(22) Filed: Oct. 18, 2006

(65) Prior Publication Data

US 2008/0095416 A1   Apr. 24, 2008

(51) Int. Cl.
*G06K 9/00* (2006.01)
*A61N 5/10* (2006.01)

(52) U.S. Cl. .................... 382/128; 382/287; 378/65

(58) Field of Classification Search ............. 382/100, 382/103, 128, 129, 130, 131, 132, 133, 134, 382/151, 168, 181, 193, 201, 232, 255, 260, 382/274, 276, 291, 294, 295, 305, 312, 287; 378/65; 600/439, 425, 411; 345/633
See application file for complete search history.

(56) References Cited

U.S. PATENT DOCUMENTS

| | | | | |
|---|---|---|---|---|
| 5,807,256 A | * | 9/1998 | Taguchi et al. | 600/425 |
| 6,307,914 B1 | * | 10/2001 | Kunieda et al. | 378/65 |
| 6,662,036 B2 | * | 12/2003 | Cosman | 600/411 |
| 6,856,324 B2 | * | 2/2005 | Sauer et al. | 345/633 |
| 6,888,919 B2 | | 5/2005 | Graf | |
| 6,973,202 B2 | * | 12/2005 | Mostafavi | 382/103 |
| 7,318,805 B2 | * | 1/2008 | Schweikard et al. | 600/439 |
| 7,343,026 B2 | * | 3/2008 | Niwa et al. | 382/103 |
| 2005/0084073 A1 | | 4/2005 | Seppi et al. | |

OTHER PUBLICATIONS

Hartley, R. et al. "The Fundamental Matrix F", Multiple View Geometry in Computer Vision,(2000) 2:241-246.
Hartley, R. et al. "Computation of the Fundamental Matrix F", Multiple View Geometry in Computer Vision,(2000) 2:279-281.
Hartley, R. et al., "The Fundamental Matrix F", Multiple View Geometry in Computer Vision, (2003) 2:241-246.
Hartley, R. et al., "Computation of the Fundamental Matrix F", Multiple View Geometry in Computer Vision, (2003) 2:279-298.

* cited by examiner

*Primary Examiner*—Seyed Azarian
(74) *Attorney, Agent, or Firm*—Vista IP Law Group, LLP.

(57) ABSTRACT

A marker system includes a marker, and a positioner coupled to the marker, the positioner configured to position the marker from a first predetermined position to a second predetermined position. A method of providing a marker system includes obtaining a first data representative of a first predetermined position, obtaining a second data representative of a second predetermined position, and moving a set of one or more markers from the first predetermined position to the second predetermined position, wherein the set of one or more markers is moved using a positioner. A method of using a marker system includes detecting a marker when the marker is located at a first position, moving the marker from the first position to a second position using a positioner, and detecting the marker when the marker is located at the second position.

39 Claims, 9 Drawing Sheets

MARKER SYSTEM AND METHOD OF USING THE SAME

FIELD

This application relates generally to marker systems, and treatment and diagnostic systems that use marker systems.

BACKGROUND

Computed tomography is an imaging procedure that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking a plurality of readings from multiple angles around the patient, relatively massive amounts of data are thus accumulated. The accumulated data are then analyzed and processed for reconstruction of a matrix (visual or otherwise), which constitutes a depiction of a density function of a volume of the bodily region being examined. By considering one or more sections in the volume, a skilled diagnostician can often diagnose various bodily ailments such as tumors, blood clots, etc.

Computed tomography has found its principal application to examination of bodily structures or the like which are in a relatively stationary condition. However, currently available computed tomographic apparatus may not be able to generate tomographic images with sufficient quality or accuracy due to physiological movement of a patient. For example, breathing has been known to cause degradation of quality in CT images. Existing CT imaging systems may use a camera to determine patient position. In such CT imaging system, a marker block having a plurality of markers is placed on a patient's chest. The camera is then used to sense the markers on the marker block. By determining the positions of the markers, a position and/or orientation of the marker block can be determined. The positional data is then considered in the construction of CT images so that patient's movement is addressed.

Existing treatment systems have also used a camera to determine a position of a patient during a treatment procedure. For example, in a radiation system, a marker block having a plurality of markers may be placed on a patient's chest. The camera is then used to sense the markers, thereby determining breathing phases and/or breathing amplitudes of the patient. The phases or amplitudes may then be used to gate a delivery of a treatment radiation beam towards a target region.

In existing systems, before the single camera is used, the camera is calibrated to determine the position of the camera. In a single camera calibration procedure, a target (e.g., a marker) position is known, and the camera is used to obtain an image of the target. The position of the camera is then estimated that will result in the image obtained by the camera. Calibration of a single camera system has been described in U.S. Pat. No. 6,973,202. Once the camera position is known, it can then be used in a tracking scheme. During a tracking scheme, the image of a target is obtained using the camera, and the position of the target is estimated that will result in the image seen by the camera. As such, in the single camera case, the scheme for tracking and the scheme for calibration are conjugate. As a result, when tracking a target from a previously calibrated camera, any systematic errors introduced by the calibration method will tend to cancel out the errors introduced by the tracking method.

Since single camera tracking tends to be insensitive for motion along the camera axis, it may be desirable to use two cameras for tracking object position using triangulation. When using dual camera system in a tracking scheme, the camera positions are known, and the two cameras are used to obtain images of a target. The position of the target is then determined using triangulation. In dual camera systems, the cameras may be calibrated by performing two single camera calibrations. However, such calibration technique is not conjugate to the tracking method, which uses triangulation. As a result, a systematic error introduced during the calibration scheme may not be offset by error introduced in the tracking scheme.

In addition, calibration methods that are used in single camera systems may not apply equally well in dual-camera systems. In particular, since in dual-camera calibration setups, the two cameras are looking simultaneously at the same calibration target, there is information about the setup that is not being utilized by an algorithm that considers the cameras to be calibrated separately. As such, it is desirable to use an algorithm that takes advantage of the intrinsic properties of a dual-camera setup for calibrating one or both of the cameras.

SUMMARY

In accordance with some embodiments, A marker system includes a marker, and a positioner coupled to the marker, the positioner configured to position the marker from a first predetermined position to a second predetermined position.

In accordance with other embodiments, a method of providing a marker system includes obtaining a first data representative of a first predetermined position, obtaining a second data representative of a second predetermined position, and moving a set of one or more markers from the first predetermined position to the second predetermined position, wherein the set of one or more markers is moved using a positioner.

In accordance with other embodiments, a method of using a marker system includes detecting a marker when the marker is located at a first position, moving the marker from the first position to a second position using a positioner, and detecting the marker when the marker is located at the second position.

In accordance with other embodiments, a method of determining a focal length includes receiving a first image obtained using the first camera, receiving a second image obtained using a second camera, determining one or more marker positions in the first image, determining one or more marker positions in the second image, and determining the focal length of the second camera using the one or more marker positions in the first image and the one or more marker positions in the second image.

In accordance with other embodiments, a computer product having a computer useable medium, the computer useable medium storing a set of instructions, an execution of which causes a process for determining a focal length to be performed, the process includes receiving a first image obtained using the first camera, receiving a second image obtained using a second camera, determining one or more marker positions in the first image, determining one or more marker positions in the second image, and determining the focal length of the second camera using the one or more marker positions in the first image and the one or more marker positions in the second image.

In accordance with other embodiments, a method of providing and/or using a marker system includes providing one or more markers, and obtaining a plurality of marker points using the one or more markers, wherein a number of the marker points is more than a number of the one or more markers.

Other aspects and features will be evident from reading the following detailed description of the embodiments.

BRIEF DESCRIPTION OF THE DRAWINGS

The drawings illustrate the design and utility of embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Various embodiments are described hereinafter with reference to the figures. It should be noted that the figures are not drawn to scale and elements of similar structures or functions are represented by like reference numerals throughout the figures. It should also be noted that the figures are only intended to facilitate the description of embodiments. They are not intended as an exhaustive description of the invention or as a limitation on the scope of the invention. In addition, an aspect described in conjunction with a particular embodiment is not necessarily limited to that embodiment and can be practiced in any other embodiments.

Figure 1:
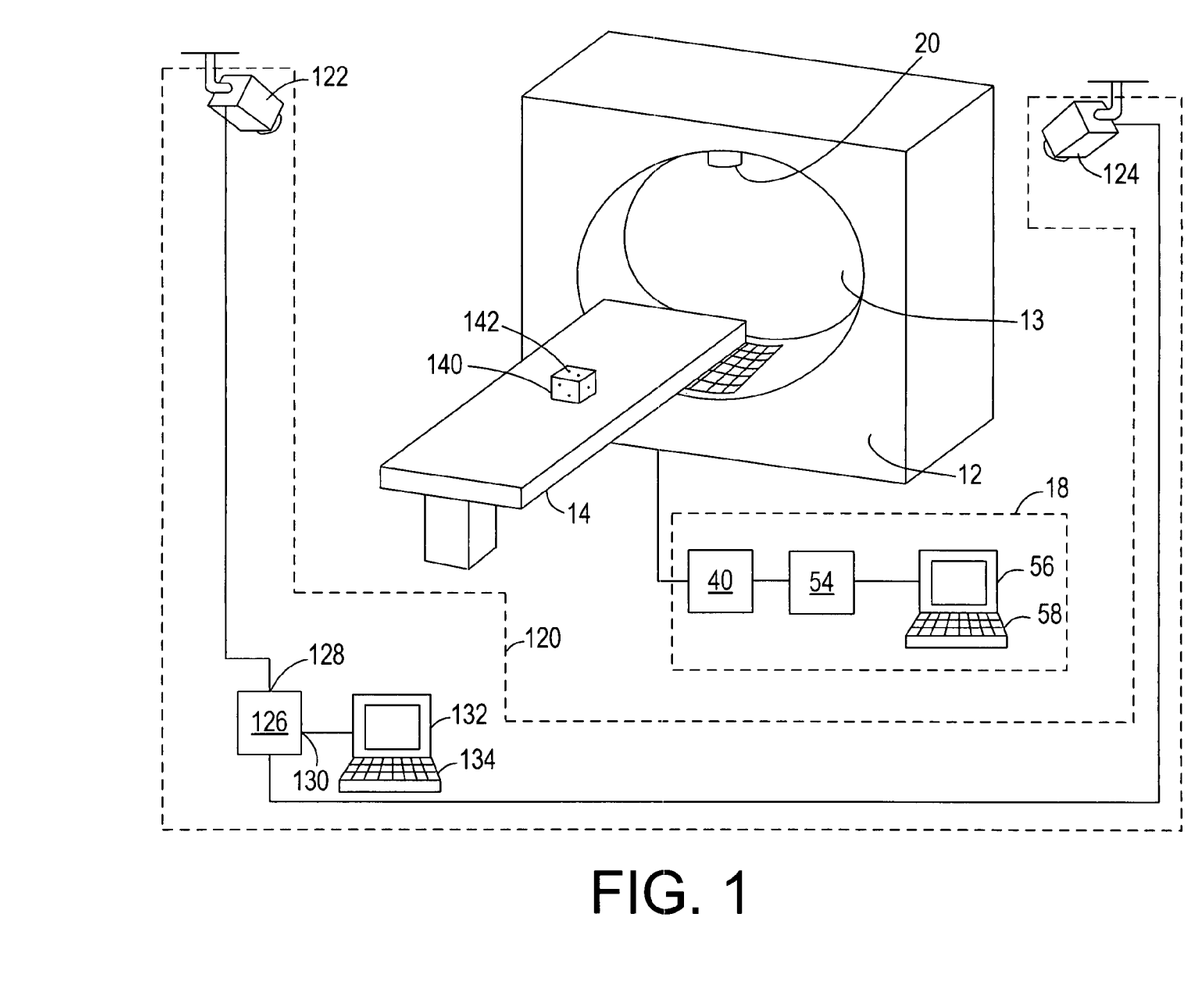
FIG. 1 illustrates a system for determining position and/or orientation of a camera in accordance with some embodiments.

FIG. 1 illustrates a radiation system 10 in accordance with some embodiments. The system 10 includes a gantry 12 having an opening (or bore) 13, a patient support 14 for supporting a patient, and a control system 18 for controlling an operation of the gantry 12. The system 10 also includes a radiation source 20 that projects a beam of radiation towards the patient while the patient is positioned at least partially within the opening 13. The radiation source 20 can be configured to generate a cone beam, a fan beam, or other types of radiation beams in different embodiments. The system 10 further includes an imager 100 located opposite from the radiation source 20.

In the illustrated embodiments, the radiation source 20 is a diagnostic radiation source for providing diagnostic energy (e.g., energy that is suitable for generating an image). In other embodiments, in addition to being a diagnostic radiation source, the radiation source 20 can also be a treatment radiation source for providing treatment energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In some embodiments, if the radiation source 20 is capable of delivering treatment energy, the system 10 can further include a collimator system (not shown) secured to the radiation source 20 for controlling a delivery of the radiation beam. In further embodiments, the radiation source 20 is a treatment radiation source configured to deliver radiation having an energy level suitable for treatment.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient, and during an imaging procedure, the gantry 12 rotates about the patient. The operation of the radiation source 20 and the gantry 12, are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54. In some embodiments, if the system 10 includes a collimator system, the operation of the collimator system is also controlled by the processor 54. In further embodiments, the control 40 also controls a position of the patient support 14. For example, the control 40 may cause the patient support 14 to translate relative to the opening 13.

In the illustrated embodiments, the imager 100 is located next to the opening 13 and opposite from the radiation source 20. In some embodiments, the imager 100 includes a conversion layer made from a scintillator element, such as Cesium Iodide (CsI), and a photo detector array (e.g., a photodiode layer) coupled to the conversion layer. The conversion layer generates light photons in response to radiation, and the photo detector array, which includes a plurality of detector elements, is configured to generate electrical signal in response to the light photons from the conversion layer. The imager 100 can have a curvilinear surface (e.g., a partial circular arc). Such configuration is beneficial in that each of the imaging elements of the imager 100 is located substantially the same distance from the radiation source 20. In an alternative embodiment, the imager 100 may have a rectilinear surface or a surface having other profiles. The imager 100 can be made from amorphous silicon, crystal and silicon wafers, crystal and silicon substrate, or flexible substrate (e.g., plastic), and may be constructed using flat panel technologies or other techniques known in the art of making imaging device. In alternative embodiments, the imager 100 may use different detection schemes. For example, in alternative embodiments, instead of having the conversion layer, the imager 100 may include a photoconductor, which generates electron-hole-pairs or charges in response to radiation.

During a diagnostic procedure, the radiation source 20 generates and directs a radiation beam 26 towards the patient, while the detector 100 measures the radiation absorption at a plurality of transmission paths defined by the radiation beam during the process. The detector 100 produces a voltage proportional to the intensity of incident radiation, and the voltage is read and digitized for subsequent processing in a computer, such as the processor 54 or another processor. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning, and/or to verify a position of a target tissue.

It should be noted that the radiation system 10 should not be limited to the configuration described previously, and that the radiation system 10 can also have other configurations in other embodiments. For example, in other embodiments, instead of a ring-configuration, the radiation system 10 can have a C-arm configuration. Also, in other embodiments, the radiation system 10 can include an arm to which the radiation source 20 is secured. In further embodiments, the radiation system 10 can have configurations that are known in the art of radiation systems.

As shown in FIG. 1, the radiation system 10 is used with, or includes, a camera system 120. The camera system 120 includes a first camera 122, a second camera 124, and a processor 126 coupled to the first and second cameras 122, 124. In the illustrated embodiments, the cameras 122, 124 are secured to a ceiling of a medical operating room, such as a radiation treatment room, or a diagnostic room. In other embodiments, the cameras 122, 124 may be secured to other objects or devices in a room, which may or may not be a medical operation room. The processor 126 includes a first input 128 for receiving image data from the first camera 122, and a second input 130 for receiving image data from the second camera 124. The camera system 120 also includes a monitor 132 for allowing a user to view information (e.g., results of computation performed by the processor 126), and an input device 134 for allowing the user to input information (e.g., constraints, variables, and values to be used by the processor 126 to perform computation). In other embodiments, the camera system 120 does not include the monitor 132 and the input device 134. Also, in further embodiments, the camera system 120 does not include the processor 126. In such cases, the cameras 122, 124 may be coupled to the processor 54, which is configured to perform the functions described herein.

In the illustrated embodiments, the camera system 120 further includes a marker block 140 having a plurality of markers 142. The marker block 140 is illustrated as having a rectangular shape. However, in other embodiments, the marker block 140 may have other shapes, such as a pyramid shape, a cone shape, a hemisphere shape, or other customized shapes. In the illustrated embodiments, the markers 142 all have a spherical shape. Alternatively, the markers 142 may have different shapes, such as an elongated shape. In further embodiments, one or more of the markers 142 may have a shape or size that is different from that of another one or more of the markers 142. The marker block 140 is so positioned such that it can be viewed by both of the first and second cameras 122, 124. The marker block 140 may used to determine a position of the second camera 124 relative to the first camera 122 in accordance with various embodiments described herein. In some embodiments, the marker block may also be used during an operation of the system 10 to determine a position of at least a portion of the patient. In other embodiments, the camera system 120 does not include the marker block 140. In such cases, other object(s) may be viewed by the cameras 122, 124, and function as the marker block 140 or the markers 142.

Figure 2:
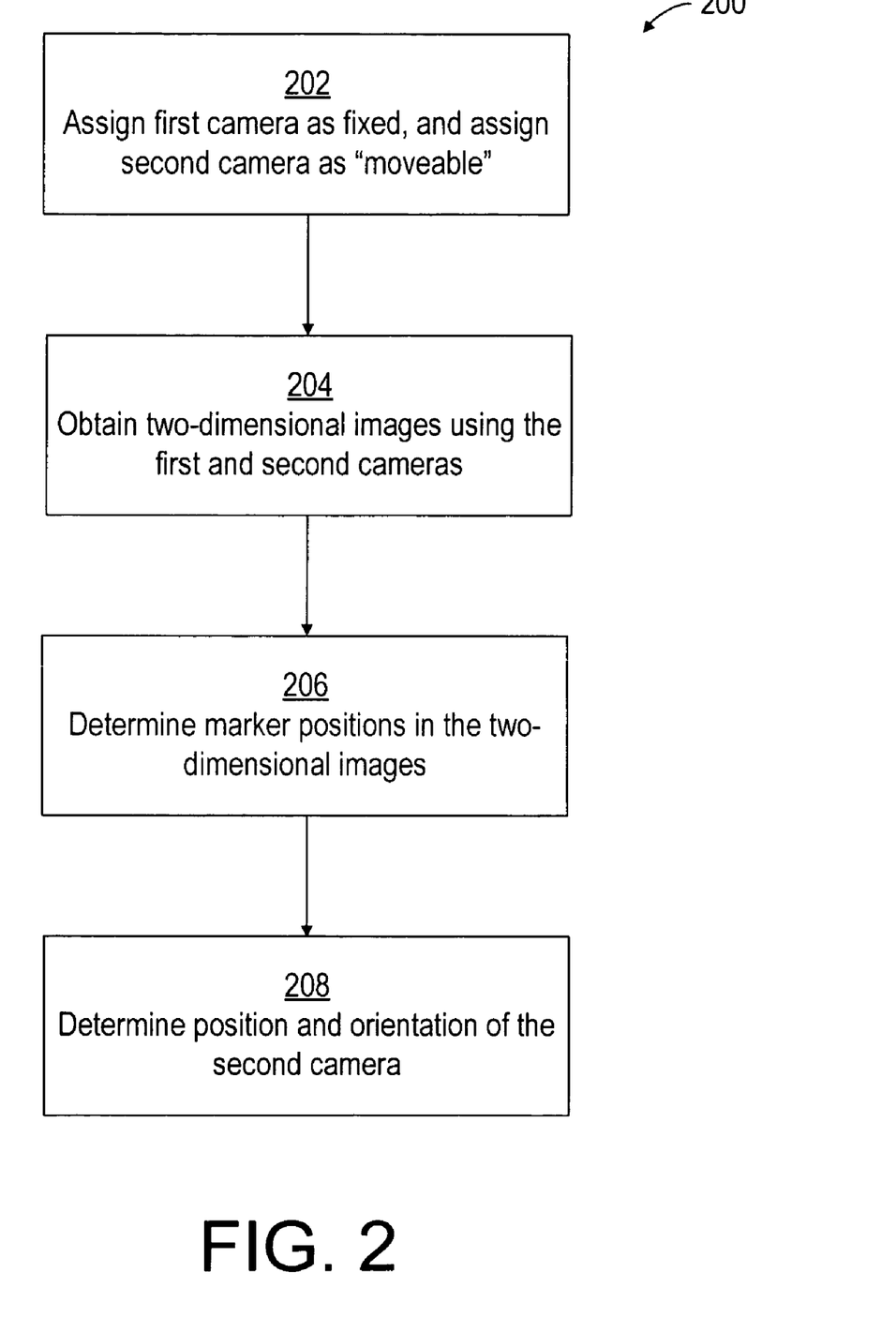
FIG. 2 illustrates a method of determining a position and/or orientation of a camera in accordance with some embodiments.

A method 200 of using the camera system 120 to determine a position of a camera in a multi-camera system in accordance with some embodiments will now be described with reference to FIG. 2. First one of the cameras 122, 124 is selected as a reference location from which the position and orientation of the other camera is based. In the illustrated example, the first camera 122 is selected as the reference location, and the position (θx, θy, θz) and orientation (θx, θy, θz) of the second camera 124 is relative to the local coordinate system (X, Y, Z) of the first camera 122. In other embodiments, the second camera 124 may be selected as the reference location.

Next, the marker block 140 is positioned such that it can be viewed by the cameras 122, 124. In the illustrated example, the marker block 140 is placed on the patient support 14 of the system 10. However, in other embodiments, the marker block 140 may be placed on other places, such as a table or a floor. The cameras 122, 124 are then used to view the marker block 140 to generate a first two-dimensional image (by the first camera 122) and a second two-dimensional image (by the second camera 124) (Step 204). The first two-dimensional image will contain images of the markers 142 as viewed by the first camera 122, and the second two-dimensional image will contain images of the markers 142 as viewed by the second camera 124. The two-dimensional images are transmitted to the processor 54/126 for processing.

The processor 54/126 receives the two-dimensional images from respective cameras 122, 124, and determines the positions of the markers as they appear in the two-dimensional images (Step 206). Various image processing techniques known in the art may be employed by the processor 54/126 to identify markers in the images. After the markers are identified in each of the two-dimensional images, the processor 54/126 can then identify the positions (e.g., relative to each image frame) of the markers as they appear in the image frame.

After the positions of the markers have been determined, the processor 54/126 then determines the position and orientation of the second camera 124 relative to the first camera 122 using the determined positions (Step 208). In the illustrated embodiments, the position of the second camera 124 is the focal point position associated with the second camera 124. However, in other embodiments, the position of the second camera 124 may be the position of other features associated with the second camera 124.

Figure 3:
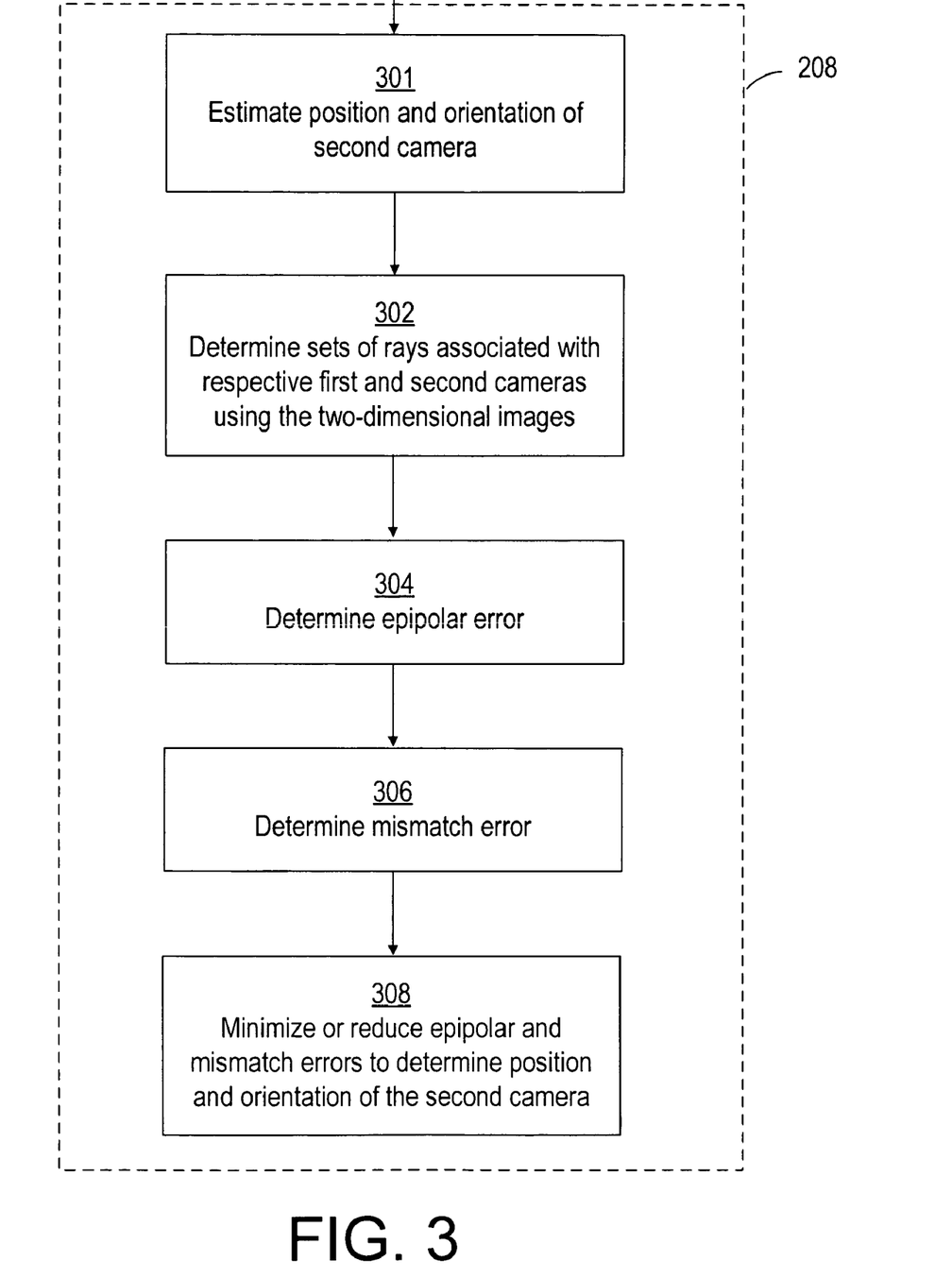
FIG. 3 illustrates a part of the method of FIG. 2 in accordance with some embodiments.

Various techniques may be employed to determine the position and orientation of the second camera 124 based on the positions of the markers in the images. FIG. 3 illustrates a technique of performing step 208 in accordance with some embodiments. First, an initial position and an initial orientation of the second camera 124 are determined (Step 301). In the illustrated embodiments, the initial position and the initial orientation of the second camera 124 are relative to the first camera 122 (e.g., the coordinate system of the first camera 122, wherein the coordinate system is assumed to be located at the focal point of the first camera 122) In the illustrated embodiments, the position and orientation of the first camera 122 (or the coordinate system of the first camera 122) may be arbitrary, since it is the "relative" position and orientation of the second camera 124 relative to the first camera 122 that are to be determined. In other embodiments, the initial position and the orientation of the second camera 124 may be relative to other object (e.g., another coordinate system, such as the coordinate system associated with the radiation system 10).

In some embodiments, the initial position and orientation of the second camera 124 may be determined by the processor 54/126 by receiving an input from a user, wherein the input represents guesses or estimates of the position and orientation of the second camera 124. For example, the user may measure the position and orientation of the housing of the second camera 124 relative to the housing of the first camera 122, and enter such data using the input device 134 into the processor 126. Because the user cannot measure the relative position of the focal point associated with the second camera 124 relative to the first focal point of the first camera 122, the inputted position by the user is an initial estimate of the location of the second camera 124 focal point.

In other embodiments, the initial position and orientation of the second camera 124 may be determined by the processor 54/126, which analyzes the second two dimensional image obtained by the second camera 124 to approximate the focal point position and orientation of the second camera 124. For example, the processor 54/126 may estimate position of the second camera 124 by determining a position of the second camera that will result in the second two dimensional image based on known position of the markers 142. Determining location of a camera by analyzing object viewed by the camera is known in the art, and will not be described in detail. Because a camera's view of an object is relatively insensitive to a change of distance along the camera's direction (e.g., the appearance of the object in the image does not change significantly by varying the distance between the camera and the object), determining the position of the second camera 124 using the above technique only provides an estimate of the position of the second camera 124.

Figure 4:
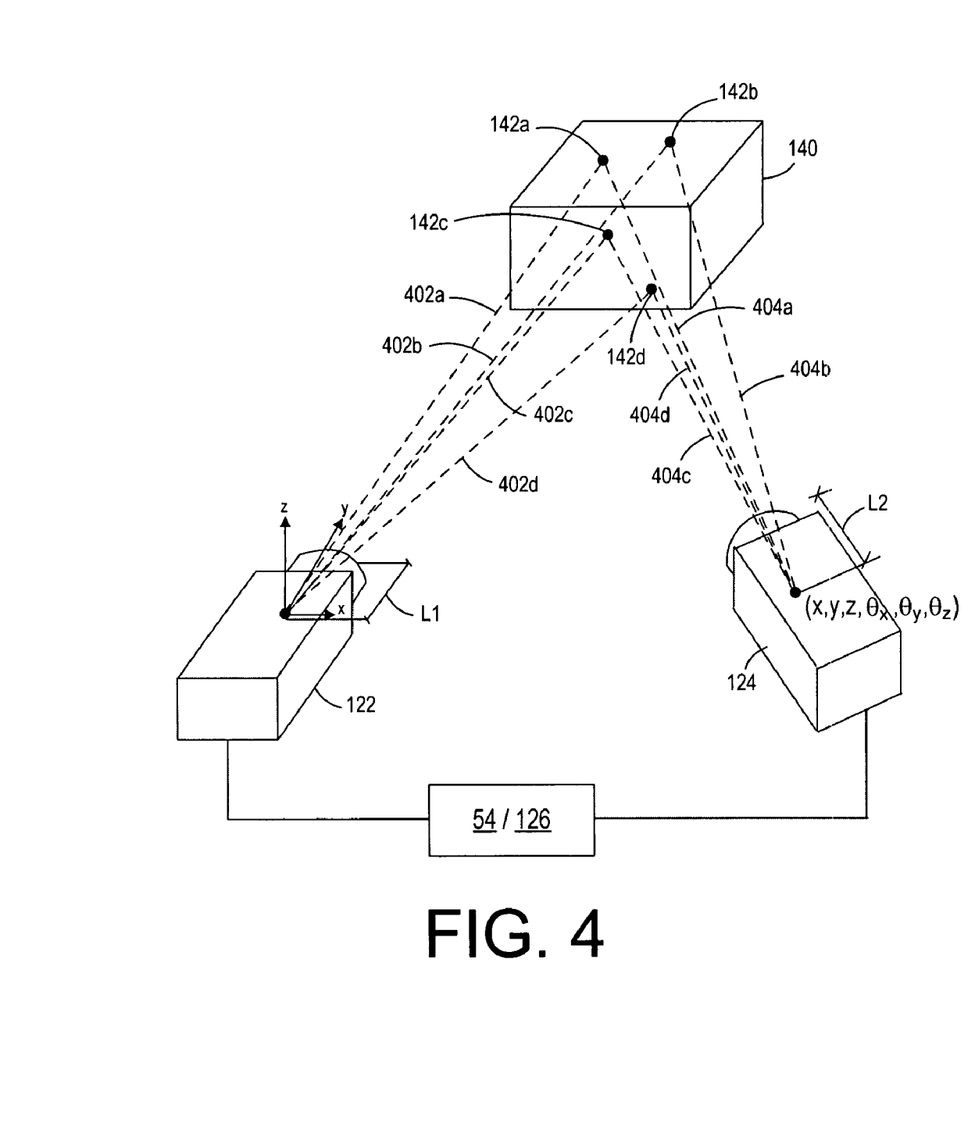
FIG. 4 is a diagram illustrating rays from two cameras.

In step 302, based on the determined marker positions in the first and second two-dimensional images from step 206, the processor 54/126 determines a first set of rays 402 associated with the first camera 122, and a second set of rays 404 associated with the second camera 124 (FIG. 4). In the illustrated embodiments, the angle (e.g., in a coordinate system fixed to the first camera 122) of rays 402 in the first set is determined by the marker positions as they appear in the first image, and the angle (e.g., in a coordinate system fixed to the second camera 124) of rays 404 in the second set is determined by the marker positions as they appear in the second image. As shown in the figure, a first set of rays 402a-402d associated with the first camera 122, and a second set of rays 404a-404d associated with the second camera 124, are created. Rays 402a and 404a correspond to the first marker 142a, rays 402b and 404b correspond to the second marker 142b, rays 402c and 404c correspond to the third marker 142c, and rays 402d and 404d correspond to the fourth marker 142d. As is known to those skilled in the art, the set of rays may be determined based on pixel size, focal length, skew (which is a measure of how non-perpendicular the pixel rows and columns are), and distortion (e.g., radial distortion). For CCDs that have square grids, there will be no skew. If any of these variables are unknown, they may be assumed or estimated.

Figure 5:
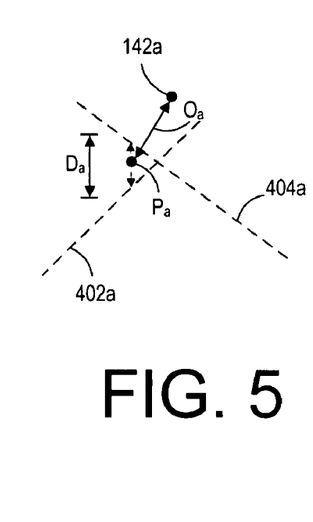
FIG. 5 illustrates an example of an epipolar error and mismatch error.

Next, the processor 54/126 determines an epipolar error (Step 304). In the illustrated embodiments, for each pair of rays (e.g., rays 402a, 404a) from the two cameras 122, 124, the processor 54/126 then computes a distance D between them. In the illustrated embodiments, the processor 54/126 is configured to calculate the shortest distance between each two pair of rays 402, 404, and use such shortest distance as the distance D. As a result, four distances Da, Db, Dc, Dd are computed for the four pair of rays 402, 404. As shown in FIG. 5, the distance D is perpendicular to both of the rays 402, 404, and is called an epipolar error. As used in this specification, the term "epipolar error" refers to a measure of how well two rays or two sets of rays correspond with each other. In some embodiments, a total epipolar error may be computed by the processor 54/126 using the distances Da, Db, Dc, and Dd. For example, the epipolar error may be computed by summing |Da|, |Db|, |Dc|, and |Dd|. Alternatively, the epipolar error may be computed by summing $Da^2$, $Db^2$, $Dc^2$, and $Dd^2$. In further embodiments, weight factor may be applied to each of the terms |D| or $D^2$ before they are summed. As such, as used in this specification, the term "epipolar error" refers to a value or a variable that is computed using one or more distance D. As shown in the illustrated embodiments, the epipolar error is a measure of how well the ray(s) 402 from the first camera 122 intersect with the ray(s) 404 from the second camera 124. For rays 402, 404 that intersect each other, the epipolar error would have a value of zero.

Next, the processor 54/126 computes a mismatch error (Step 306). A mismatch error is a measure of how well the intersections (or approximated intersections if the rays do not intersect) between rays 402, 404 match up with the actual position of the marker(s). Various techniques may be used to determine the mismatch error. In the illustrated embodiments, for each pair of rays (e.g., rays 402a, 404a), a cross point P is determined. As a result, four cross points Pa, Pb, Pc, and Pd are determined. As shown in FIG. 5, each cross point P may be calculated as the midpoint of the shortest line that span between the rays 402, 404. If the rays 402, 404 intersect each other, the cross point P will be the point of intersection. The processor 54/126 then computes the optimal position of the marker block 140 such that the offset O between P and the corresponding marker position for each of the markers 142 is minimized. This minimized offset O is used for the mismatch error. As such, offset Oa would be the minimized distance between Pa, which is the cross point associated with rays 402a, 404a, and the marker 142a; offset Ob would be the minimized distance between Pb, which is the cross point associated with rays 402b, 404b, and the marker 142b; offset Oc would be the minimized distance between Pc, which is the cross point associated with rays 402c, 404c, and the marker 142c; and offset Od would be the minimized distance between Pd, which is the cross point associated with rays 402d, 404d, and the marker 142d. The determination of the offsets Oa, Ob, Oc, and Od is subject to the constraint that the markers 142 maintain a rigid body relationship.

In some embodiments, a total mismatch error may be computed by the processor 54/126 using the offsets Oa, Ob, Oc, and Od. For example, the mismatch error may be computed by summing |Oa|, |Ob|, |Oc|, and |Od|. Alternatively, the mismatch error may be computed by summing $Oa^2$, $Ob^2$, $Oc^2$, and $Od^2$. In further embodiments, weight factor may be applied to each of the terms |O| or $O^2$ before they are summed. As such, as used in this specification, the term "mismatch error" refers to a value or a variable that is computed using one or more offsets O.

The processor 54/126 next minimizes, or at least reduces, the epipolar error and the mismatch error calculated from steps 304, 306 (Step 308). For example, the processor 54/126 may adjust the estimated or calculated position and orientation of the second camera 124, and repeat steps 302-306, until the epipolar error and the mismatch error are minimized, or reach a prescribed threshold. The processor 54/126 may be configured to adjust the estimated or calculated position and orientation of the second camera 124 using various techniques known in the art. For example, in some embodiments, this can be accomplished by minimizing the errors with respect to each of the second camera 124 6DOF parameters successively using Brent's method (or other suitable one-dimensional minimization scheme), and iterating until the global minimum is reached. A direction set method, which is known in the art, can be used to speed up computation by guessing directions in parameter space that will converge to the minimum more rapidly. The advantage of this minimization scheme is that no derivatives in parameter space need to be calculated. In some embodiments, the epipolar error and the mismatch error may be combined (e.g., by adding them, or by adding them after they are multiplied by respective weight factors—i.e., Total error=a (epipolar error)+b (mismatch error)) to obtain a total error. The weight factors a, b may be any values selected by a user. For example, the ratio a/b may be approximately 0.01, or other values. In such cases, the processor 54/126 are configured to adjust the estimated or calculated position and orientation of the second camera 124 until the total error is minimized or at least reaches a prescribed limit (e.g., 0.1 cm or 0.01 $cm^2$). In other embodiments, the epipolar error and the mismatch error are not combined. In such cases, an epipolar error limit and a mismatch error limit may be prescribed (e.g., by the user inputting these limits into the processor 54/126). The processor 54/126 are configured to adjust the estimated or calculated position and orientation of the second camera 124 until the conditions that (1) epipolar error (or a weighted epipolar error) reaches the prescribed epipolar error limit, and (2) the mismatch error (or a weighted mismatch error) reaches the prescribed mismatch error limit, are achieved.

In other embodiments, derivative(s) may be used to calculate the next guess for the second camera 124's six degree-of-freedom parameters. For example, a conjugate gradient method or other techniques known in the art may be used to estimate the second camera 124's position and orientation.

In further embodiments, instead of using an iterative process to determine the position and orientation of the second camera 124, the processor 54/126 may be configured to solve a set of equations to determine the position and orientation of the second camera 124. For example, the position (x, y, z) and orientation (θx, θy, θz) of the second camera 124 may be variables that are used to express equations of the rays 402, 404, and equations for the epipolar error and mismatch error. In such cases, the step 301 of obtaining initial estimates of the position and orientation of the second camera 124 is not needed. Also, in such cases, the step 302 of determining rays 402, 404 would be performed by the processor 54/126 by determining a set of equations that represent the sets of rays 402, 404, which are expressed using the variable position and variable orientation of the second camera 124. Similarly, the step 304 of determining the epipolar error and the step 306 of determining the mismatch error would be performed by the processor 54/126, which determines equations that represent the epipolar error and the mismatch error, wherein the equations are expressed using the variable position and variable orientation of the second camera 124. Using such technique, the step 308 of minimizing the epipolar error and the mismatch error may be performed by determining a derivative of the epipolar error equation and a derivative of the mismatch error equation, and solving for the unknown variables expressed in the two derivative equations and the ray equations. In the illustrated embodiments, the processor 54/126 is configured to solve a set of equations to determine the six unknown variables (x, y, z, θx, θy, θz). In other embodiments, the epipolar error equation and the mismatch error equation may be combined. For example, the epipolar error (or a weighted epipolar error) may be added to the mismatch error (or a weighted mismatch error) to obtain a total error. In such cases, a derivative of the equation representing the total error may be obtained, and is then used with other equations (e.g., the ray equations) to solve for the unknown variables.

In the above embodiments, the processor 54/126 is configured to determine the position and orientation (x, y, z, θx, θy, θz) of the second camera 124 relative to the first camera 122. In other embodiments, the processor 54/126 may also be configured to determine the focal length associated with the first camera 122 and/or the second camera 124. For example, the focal length L1 of the first camera 122 and the focal length L2 of the second camera 124 may be set as variables for the processor 54/126 to solve. In such cases, the ray equations described herein may be expressed using the focal length variables L1, L2, which will be solved using the processor 54/126. The number of markers 142 may be increased to allow the processor 54/126 to determine additional equations for solving the additional variables L1, L2. In the illustrated embodiments, the number of markers may be a value that is between 4 and 12, inclusive, and more preferably, a value that is between 4 and 6, inclusive.

It should be noted that in other embodiments, one or more steps described with reference to FIGS. 2 and 3 may be combined with another step in the method 200. In other embodiments, any of the steps described with reference to FIGS. 2 and 3 may be further divided into sub-steps. Also, in further embodiments, one or more of the steps described with reference to FIGS. 2 and 3 may not be included. For example, in some embodiments, the method 200 does not include the step 304 of determining the epipolar error, or the step 306 of determining the mismatch error. In further embodiments, instead of determining both the position and the orientation of the second camera 124, the processor 54/126 is configured to determine either the position or the orientation of the second camera 124. In still further embodiments, one or more of the variables x, y, z, θx, θy, θz, L1, L2 may be known or assumed to have value. In such cases, the number of unknown variables that need to be solved by the processor 54/126 would be reduced, thereby increasing the computing efficiency of the processor 54/126.

In the above embodiments, the cameras 122, 124 are adapted to view the marker block 140 which includes a plurality of markers 142. The markers 142 provide a plurality of constraint equations that may be used by the processor 54/126 to solve a set of unknown variables. In other embodiments, instead of using a marker block 140 that includes a sufficient number of markers 142 for allowing the processor 54/126 to solve for all of the unknown variables, the marker block 140 may include an insufficient number of markers 142. For example, the marker block 140 may include one or two markers 142. In such cases, the marker block 140 may be positioned to a plurality of known positions to thereby allow a sufficient number of constraint equations to be determined by the processor 54/126. For example, the marker block 140 may be placed in a first known position, and the cameras 122, 124 are used to determine two-dimensional images of the markers 142 while the marker block 140 is at the first known position. Next, the marker block 140 is placed in a second known position, and the cameras 122, 124 are used to determine additional two-dimensional images of the markers 142 while the marker block 140 is at the second known position. In such cases, the pixel positions of the marker captured at different stage positions may be combined as a set of point locations. This allows the generation of a calibration "object" using a plurality of marker points without worrying about overlapping of markers in any view. The technique described above with reference to FIGS. 2 and 3 are then similarly performed to determine the position and/or orientation of the second camera 124, and/or the focal lengths L1, L2 of the respective cameras 122, 124.

In the above embodiments, the marker block 140 are placed in two known positions. In alternative embodiments, the positioning of the marker block 140, and the obtaining of the two-dimensional images of the markers 142 at the respective known positions, may be continued until a desired number of two-dimensional images are obtained by the cameras 122, 124.

Figure 6:
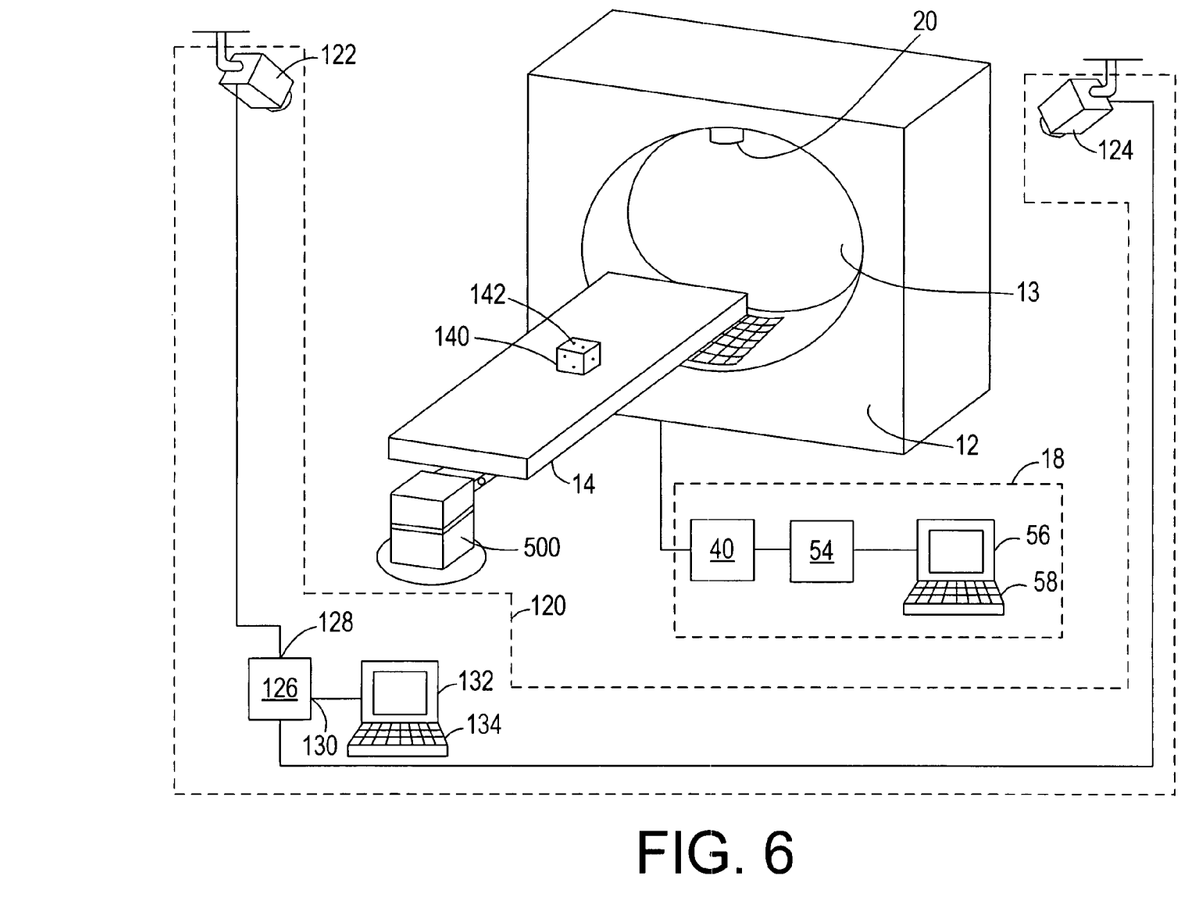
FIG. 6 illustrates a system for determining position and/or orientation of a camera in accordance with other embodiments.

In some embodiments, the marker block 140 may be placed on the patient support 14 that is coupled to a positioner 500 (FIG. 6). In such cases, the positioner 500 may be used to place the marker block 140 to known positions. For example, the positioner 500 may translate along the Z-direction, the Y-direction, and/or the X-direction. If the positioner 500 is capable of rotating/tilting the patient support 14, it may also rotate the patient support 14 to thereby place the marker block 140 to a plurality of known positions. Patient support positioning devices have been described in U.S. patent application Ser. No. 11/415,974, entitled "Patient Support Systems", the entire disclosure of which is expressly incorporated by reference herein. In further embodiments, instead of using the patient support 14, any of other types of positioning devices may be used to position the marker block 140. In further embodiments, the marker block 140 is not needed. In such cases, the marker(s) 142 may be placed or coupled to the positioner directly. In still further embodiments, the marker(s) 142 may be a component or a feature of the positioner.

FIG. 7 illustrates a marker system that provides a desired number of marker reference locations using a number of markers that is less than the desired number. In the illustrated embodiments, the marker block has one marker 142 attached thereto, and the marker block is coupled to the patient support 14. The marker 142 is initially placed at a first predetermined location (FIG. 7A). The placement of the marker 142 at the first predetermined location may be performed using the positioner 500, or alternatively, by an operator manually. In some embodiments, the positioner 500 may be controlled by a processor, such as processor 54, which receives data from a memory regarding the first predetermined location. The processor 54 then causes the positioner 500 to position the patient support 14, thereby placing the marker 142 at the first predetermined location. Alternatively, a user may input data representative the first predetermined location to the processor 54.

Figure 7A:
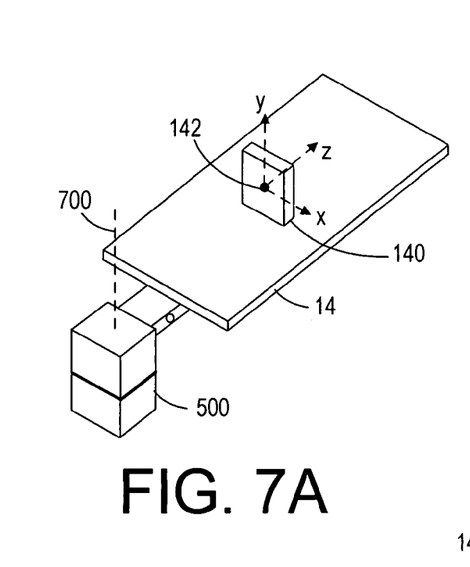
FIGS. 7A-7D illustrate a marker system in accordance with some embodiments.
Figure 7B:
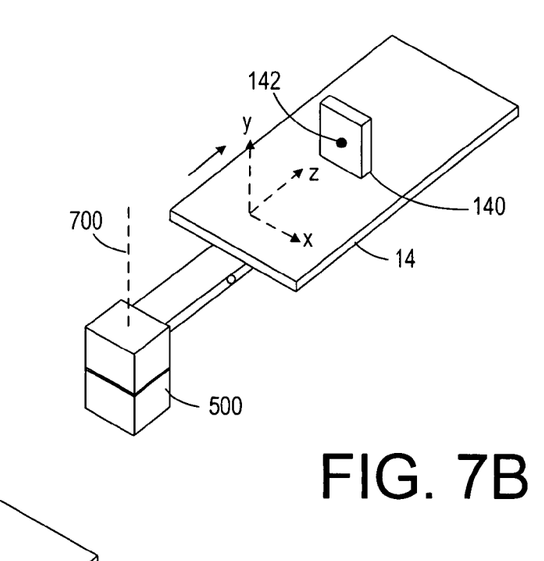

In the illustrated embodiments, the processor coupled to the positioner 500 is configured to cause the positioner to place the marker 142 at a second predetermined location (FIG. 7B). As shown in the example, the positioner 500 places the marker 142 at the second predetermined location by translating the patient support 14 in a Z-direction. As similarly discussed, the second predetermined location may be obtained by the processor 54 from a memory, or by a user entering data for the processor 54.

Figure 7C:
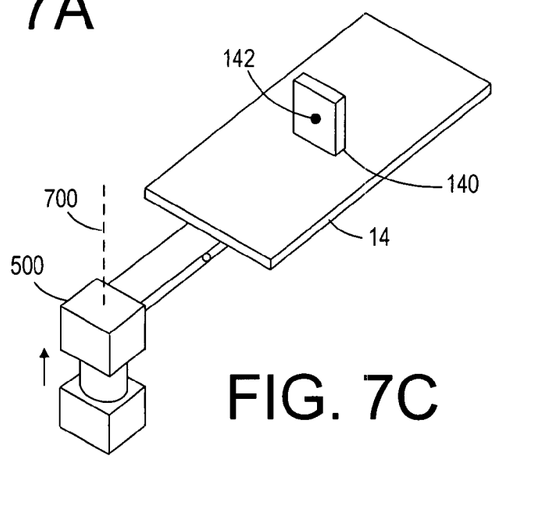

The processor coupled to the positioner 500 is also configured to cause the positioner to place the marker 142 from the second predetermined location to a third predetermined location (FIG. 7C). As shown in the example, the positioner 500 places the marker 142 at the third predetermined location by translating the patient support 14 in a Y-direction. As similarly discussed, the third predetermined location may be obtained by the processor 54 from a memory, or by a user entering data for the processor 54.

Figure 7D:
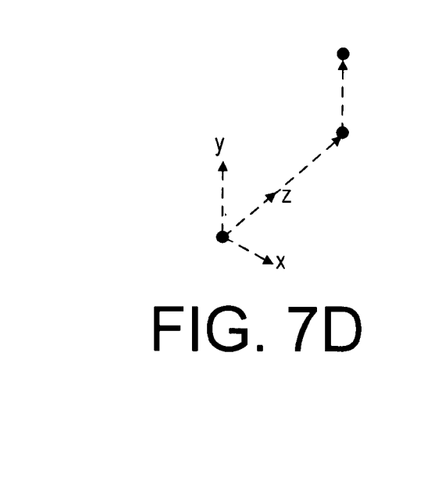

FIG. 7D illustrates a collection of the marker 142 positions from FIGS. 7A-7C. As shown in the figure, by positioning the marker 142 at known/predetermined locations, a virtual calibration object having a desired number (3 in the example) of marker reference points can be created, wherein the desired number is less than a number (1 in the example) of actual marker 142. An advantage of this is that one can effectively create a very large calibration object, which results in a more accurate calibration, with a small calibration block.

In other embodiments, instead of, or in addition to, moving the marker 142 in a rectilinear path, the positioner 500 can move the marker 142 in other paths, such as a curvilinear path. For example, in other embodiments, the positioner 500 may rotate the marker 142 about axis 700 to place the marker 142 at know position(s).

In any of the embodiments described herein, after the position and orientation of the second camera 124 are determined, the camera system 120 may then be used in a medical procedure, such as a diagnostic procedure, a treatment planning procedure, or a treatment procedure. For example, the camera system 120 may be used with the radiation system 10, wherein the cameras 122, 124 are used to sense a position of a marker block (e.g., block 140) rested above a patient's chest while the patient is being imaged by the radiation system 10. In the illustrated embodiments, the marker block position may be determined by triangulation technique, in which the position of the marker block is triangulated using positional data (e.g., images of the markers 142) obtained by the cameras 122, 124, and the relative position and orientation of the second camera 124 relative to the first camera 122 as determined using techniques described herein. In some embodiments, the sensed position of the marker block may be used to determine breathing amplitudes of the patient who undergoes respiratory cycles. In other embodiments, the sensed position of the marker block may also be used to determine a phase of respiratory cycle. In some cases, the determined amplitudes and/or phases of the respirator cycle may be used to determine a radiation treatment plan, which prescribes criteria for gating a delivery of a radiation beam to treat a portion of the patient.

In the above embodiments, the technique is described with reference to determining the position and orientation of the second camera. In other embodiments, the same technique may also be used to determine the position and orientation of the first camera. Also, instead of determining a position and orientation of one camera relative to another camera, the position and orientation of a camera may be determined with reference to another object, such as a part of a room, a treatment device, a diagnostic device, or a patient support.

Although the camera system 120 has be described as being used with the radiation system 10, in other embodiments, the camera system 10 may be used with other devices. For example, in other embodiments, the camera system 120 may be used with a MR system for generating MR images, a PET system for generating PET images, or a SPECT system for generating SPECT images, or other types of imaging systems. In further embodiments, the camera system 120 may be used with a diagnostic machine, a simulator, an inspection machine, or another machine that may or may not be for medical use. In any of these embodiments, the position and orientation of a camera may be determined relative to the other camera, or relative to any of these devices/machines (e.g., MR system, PET system, SPECT system, diagnostic machine, simulator, inspection machine, and other machines). In further embodiments, the marker system may be used to calibrate and/or set up patient support, positioner, and radiation machine.

Although the marker system has been described with reference to determining calibration data for a camera, in other embodiments, the marker system may be used for other purposes.

Figure 8A:
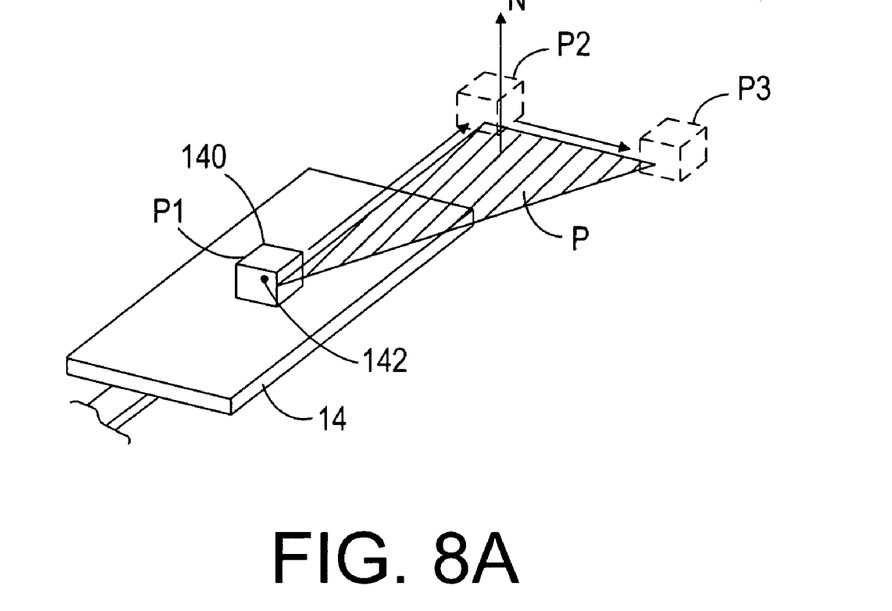
FIG. 8A-8D illustrate different applications of a marker system in accordance with some embodiments.

FIG. 8A illustrates a technique of determining a movement plane for the patient support 14 using an embodiment of the marker system. In the illustrated example, the marker block 140 is placed on the patient support 14 such that the marker block 140 is located at position P1. The patient support 14 is then moved to place the marker block 140 at position P2. Next, the patient support 14 is moved again to place the marker block 140 at position P3. At each of the positions, P1, P2, P3, a camera is used to capture an image of the marker block 140, and the image is analyzed to determine a position of the marker block 140 relative to a reference point. After the positions of the marker block 140 at P1, P2, P3 have been determined, a plane P defined by the positions P1, P2, P3 can then be determined. The plane P represents a plane in which the patient support 14 moves. In some cases, the plane P may be represented by a normal vector N that is perpendicular to the plane P. Although only three positions P1-P3 are used in the example, in other embodiments, the marker block 140 may be placed at more than three positions. In such cases, the plane P may be determined as the plane that best fit among the points corresponding to the plurality of positions. In the example, the marker block 140 has one marker 142 attached thereto. However, in other embodiments, the marker block 140 can have a plurality of markers 142. Also, in other embodiments, instead of using a marker block, part of the patient support 14, or a marked area of the patient support 14, may be used as a marker. Further, any of the embodiments of the marker block or marker described herein may be used.

Figure 8B:
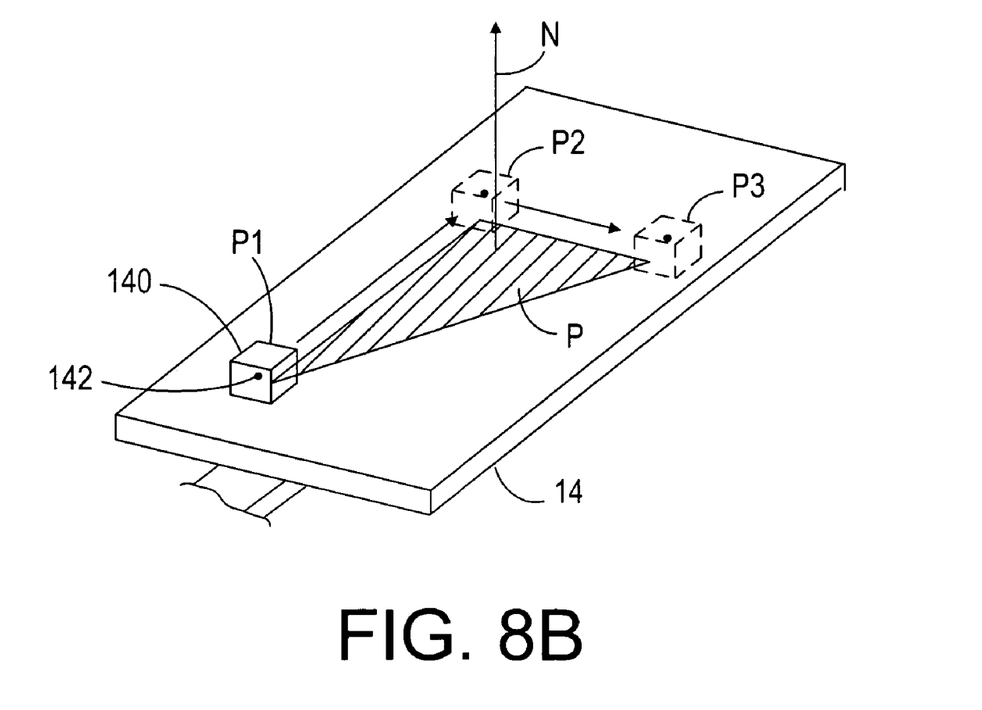

FIG. 8B illustrates a technique of determining a plane of the patient support 14 using an embodiment of the marker system. In the illustrated example, the marker block 140 is placed on the patient support 14 such that the marker block 140 is located at position P1 relative to the patient support 14. The marker block 140 is then moved to position P2 relative to the patient support 14. Next, the marker block 140 is moved again to position P3 relative to the patient support 14. In such cases, the movement of the marker block 140 may be performed manually or using a device, such as a robotic arm. At each of the positions, P1, P2, P3, a camera is used to capture an image of the marker block 140, and the image is analyzed to determine a position of the marker block 140 relative to a reference point. After the positions of the marker block 140 at P1, P2, P3 have been determined, a plane P defined by the positions P1, P2, P3 can then be determined. In one embodiment, the plane P can be determined using principal component analysis. The plane P represents a plane of the patient support 14. In some cases, the plane P may be represented by a normal vector N that is perpendicular to the plane P. Although only three positions P1-P3 are used in the example, in other embodiments, the marker block 140 may be placed at more than three positions. In such cases, the plane P may be determined as the plane that best fit among the points corresponding to the plurality of positions. In the example, the marker block 140 has one marker 142 attached thereto. However, in other embodiments, the marker block 140 can have a plurality of markers 142. Also, in other embodiments, instead of using a marker block, part of the patient support 14, or a marked area of the patient support 14, may be used as a marker. Further, any of the embodiments of the marker block or marker described herein may be used.

Figure 8C:
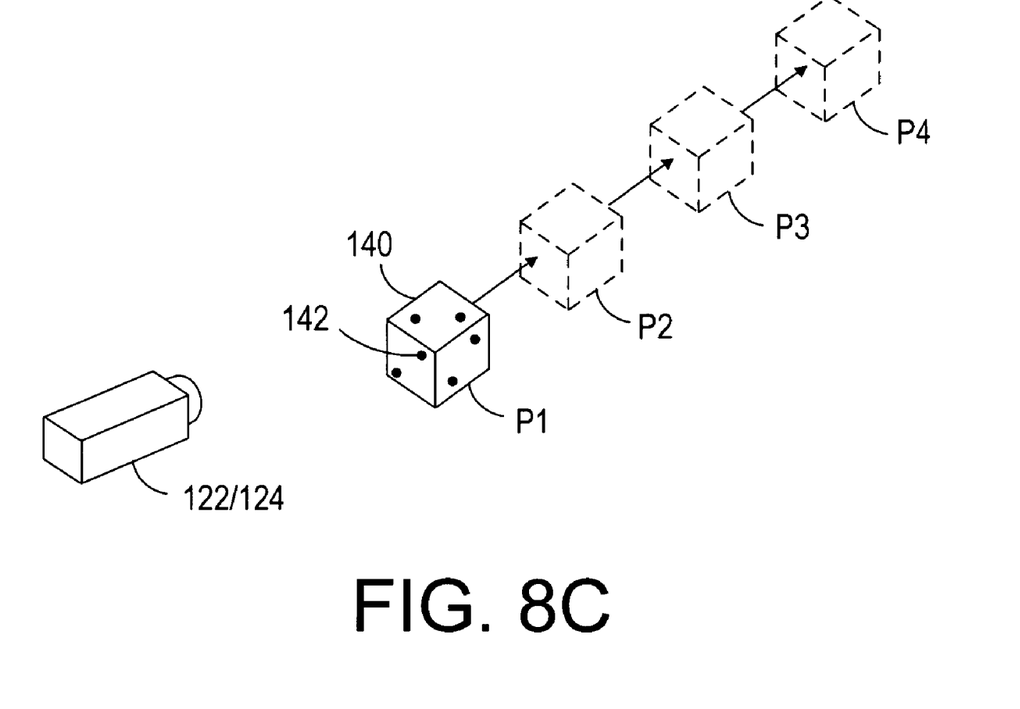

FIG. 8C illustrates a technique of determining a focal length of a camera (e.g., camera 122 or 124). First, the marker block 140 is placed at a first position P1. The marker block 140 is then moved to positions, P2, P3, and P4. At each of the positions P1-P4, a camera is used to capture an image of the marker block 140, and the image is analyzed to determine a position of the marker block 140 relative to a reference point. The focal length of the camera 122/124 is then determined using the determined positions by comparing how the apparent size of a feature (distance between two markers, width of a marker block, or width of a marker) in the image decreases with increasing distance. The equations to solve for the focal length are easily established by one skilled in the art based on the pinhole camera model. In the illustrated embodiment, the marker block 140 is progressively moved further away from the camera 122/124. This allows the focal length of the camera 122/124 to be determined more accurately. In the example, the marker block 140 is placed at four positions P1-P4. In other embodiments, the marker block 140 may be placed at less than four positions, or more than four positions. In the example, the marker block 140 has six markers 142 attached thereto. However, in other embodiments, the marker block 140 can have other numbers of markers 142. Also, in other embodiments, instead of using a marker block, part of the patient support 14, or a marked area of the patient support 14, may be used as a marker. Further, any of the embodiments of the marker block or marker described herein may be used.

Figure 8D:
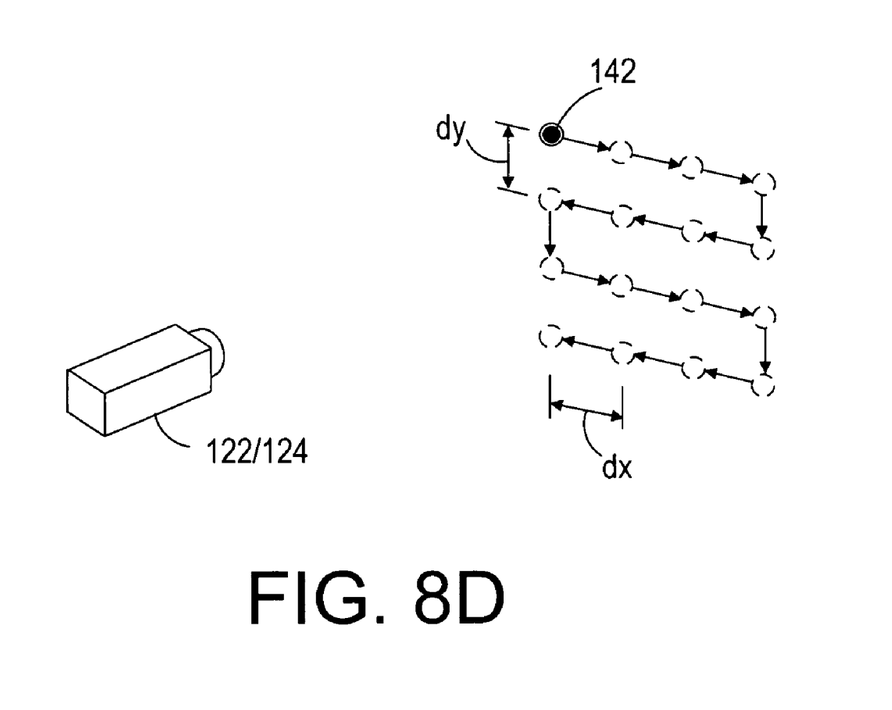

FIG. 8D illustrates a technique of determining an image aspect ratio associated with a camera (e.g., camera 122 or 124). In the illustrated embodiment, marker 142 is positioned to a plurality of known positions to thereby form a grid of reference locations. In the example, the grid is arranged in columns and rows, in which each two adjacent columns are spaced at dx, and each two adjacent rows are spaced at dy. When the marker 142 is at each of the reference locations, a camera is used to capture an image of the marker 142, and the image is analyzed to determine a position of the marker 142 relative to a reference point. The images of the markers at different locations are then combined or superimposed to thereby form a composite image that includes an image of a grid of markers. In the composite image, the grid of markers may have column spacing at dx' and row spacing dy'. In some cases, an aspect ratio AR may be determined (=dx'/dy' or dy'/dx') and is then compared to a reference ratio (=dx/dy or dy/dx). Alternatively, the column spacing dx' may be normalized first by dividing dx' by dx, and the row spacing dy' may be normalized first by dividing dy' by dy. The normalized column spacing Ndx and the normalized row spacing Ndy may be used to determine an aspect ratio (=Ndx/Ndy or Ndy/Ndx). In some embodiments, the determined aspect ratio may be used in a medical procedure, such as in a treatment procedure or a diagnostic procedure. For example, the aspect ratio may be used to correct image distortion of an image of a portion of a patient. Alternatively, the determined aspect ratio may be used in a non-medical procedure. In the illustrated embodiment, the camera is aimed at a direction that is approximately perpendicular to a plane defined by the plurality of reference locations. In other embodiments, the camera may be aimed at a different direction.

As shown in FIGS. 8A-8D, by positioning the marker 142 at known/predetermined locations, a virtual calibration object having a desired number of marker reference points can be created, wherein the desired number is less than a number of actual marker 142.

In any of the embodiments described herein, the positioning of the marker(s) or marker block needs not be performed using the patient support 14, and may be performed using other devices. For example, the marker block or marker(s) may be positioned using a robotic arm. In other embodiments, the marker block or marker(s) may be coupled to a rotating gantry of a radiation machine (e.g., a radiation treatment machine or a radiation diagnostic machine). Also, in any of the embodiments described herein, portion(s) of a patient support, portion(s) of a gantry, portion(s) of a positioner, or portion(s) of other non-marker devices, may be used as marker(s). Further, any of the embodiments of the marker system described herein may be used for medical or non-medical purposes.

Computer System Architecture

Figure 9:
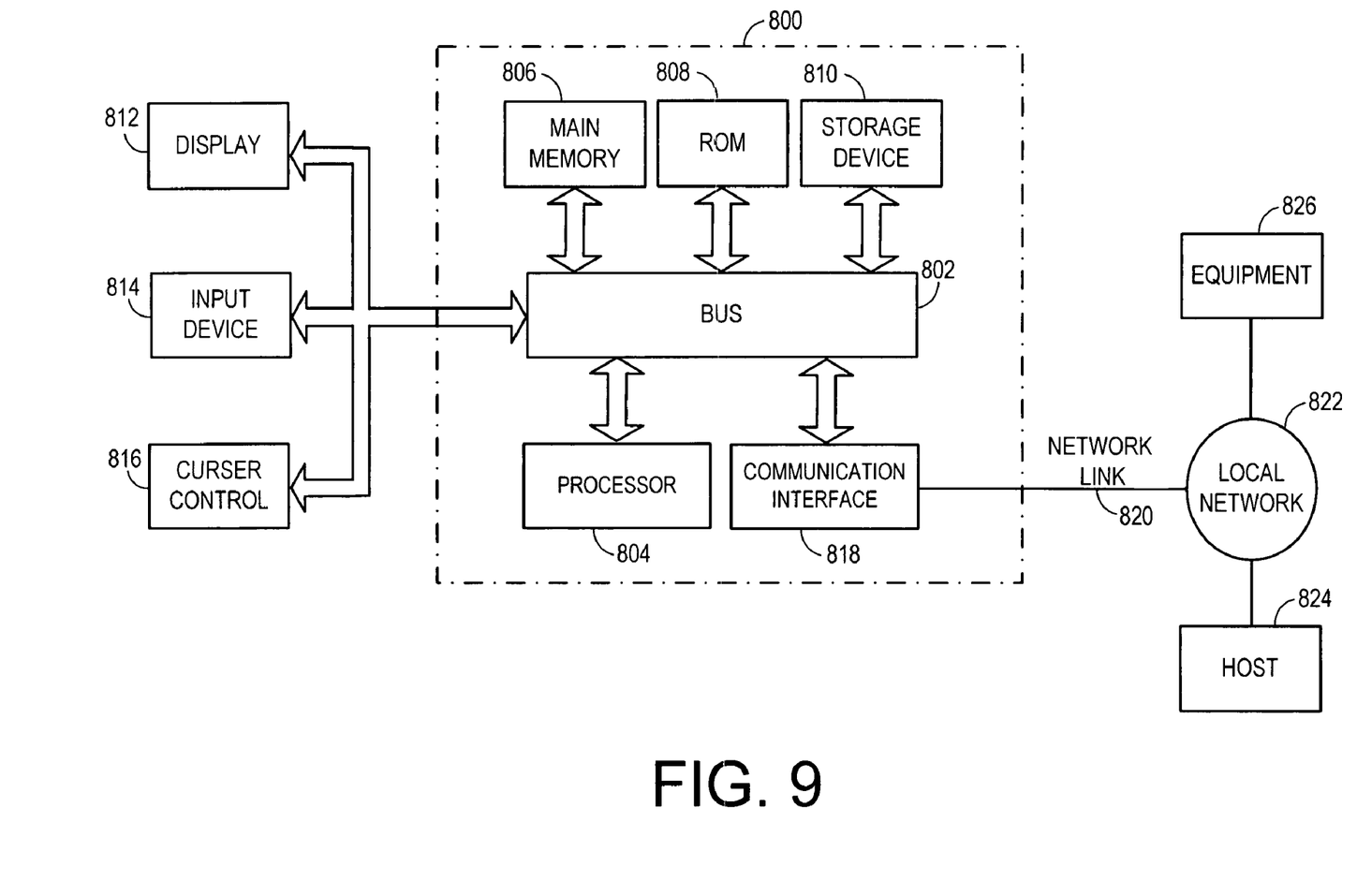
FIG. 9 illustrates a block diagram of a computer system that can be used to perform various functions described herein in accordance with some embodiments.

FIG. 9 is a block diagram illustrating an embodiment of a computer system 800 that can be used to perform various functions described herein. Computer system 800 includes a bus 802 or other communication mechanism for communicating information, and a processor 804 coupled with the bus 802 for processing information. The processor 804 may be an example of the processor 54, or alternatively, an example of a component of the processor 54, of FIG. 1. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 812 (which may be display 56), such as a cathode ray tube (CRT), for displaying information to a user. An input device 814, including alphanumeric and other keys (e.g., input device 58), is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

In some embodiments, the computer system 800 can be used to perform various functions described herein. According to some embodiments of the invention, such use is provided by computer system 800 in response to processor 804 executing one or more sequences of one or more instructions contained in the main memory 806. Those skilled in the art will know how to prepare such instructions based on the functions and methods described herein. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826, such as any of the devices herein (e.g., device 166, system 10, patient support system 200, etc.), or a switch operatively coupled to any of the devices described herein. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network(s), the network link 820, and the communication interface 818.

Although particular embodiments have been shown and described, it will be understood that it is not intended to limit the claimed inventions, and it will be obvious to those skilled in the art that various changes and modifications may be made without departing from the spirit and scope of the application. For example, in other embodiments, the camera system 120 may not include one or more of the components described herein. Also, the operations performed by the processor 54/126 can be performed by any combination of hardware and software, and should not be limited to particular embodiments comprising a particular definition of "processor." In addition, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A marker system, comprising:
   a marker; and
   a positioner coupled to the marker, the positioner configured to position the marker from a first predetermined position to a second predetermined position, wherein the first and second predetermined positions provide a virtual marker system having a first marker point at the first predetermined position and a second marker point at the second predetermined position;
   wherein the positioner is further configured to position the marker from the second predetermined position to a third predetermined position.

2. The marker system of claim 1, wherein the positioner comprises a patient support.

3. The marker system of claim 1, wherein the positioner is configured to move the marker in a rectilinear direction.

4. The marker system of claim 1, wherein the positioner is configured to move the marker in a curvilinear direction.

5. The marker system of claim 1, further comprising a block to which the marker is secured, wherein the positioner is configured to move the block.

6. The marker system of claim 5, further comprising one or more additional markers secured to the block.

7. The marker system of claim 1, further comprising a memory storing the first and second predetermined positions.

8. The marker system of claim 7, further comprising a processor coupled to the memory and the positioner.

9. A method of providing a marker system, comprising:
   obtaining a first data representative of a first predetermined position;
   obtaining a second data representative of a second predetermined position;
   moving a set of one or more markers from the first predetermined position to the second predetermined position, wherein the set of one or more markers is moved using a positioner, and wherein the first and second predetermined positions provide a virtual marker system having a first marker point at the first predetermined position and a second marker point at the second predetermined position; and
   moving the set of one or more markers from the second predetermined position to a third predetermined position.

10. The method of claim 9, wherein the first and second data are obtained from a user.

11. The method of claim 9, wherein the first and second data are obtained from a memory that stores the first and second data.

12. The method of claim 9, wherein the set of one or more markers is coupled to a patient support.

13. The method of claim 9, wherein the set of one or more markers are secured to a marker block, and the set of one or more markers are moved by moving the marker block.

14. The method of claim 9, wherein the set of one or more markers comprises a plurality of markers.

15. The method of claim 9, further comprising positioning the first set of one or more markers at the first predetermined position.

16. The method of claim 9, further comprising obtaining a third data representative of a third predetermined position.

17. A method of using a marker system, comprising:
   detecting a marker when the marker is located at a first predetermined position;
   moving the marker from the first predetermined position to a second predetermined position using a positioner, wherein the first and second predetermined positions provide a virtual marker system having a first marker point at the first predetermined position and a second marker point at the second predetermined position;
   detecting the marker when the marker is located at the second predetermined position; and
   moving the marker from the second predetermined position to a third predetermined position.

18. The method of claim 17, wherein the marker is coupled to a patient support.

19. The method of claim 17, further comprising moving the marker to the first position.

20. The method of claim 17, further comprising detecting the marker when the marker is located at the third predetermined position.

21. The method of claim 17, further comprising:
   determining a first coordinate of the marker when the marker is at the first predetermined position; and
   determining a second coordinate of the marker when the marker is at the second predetermined position.

22. The method of claim 21, further comprising storing the first and second coordinates in a medium.

23. A system that uses a marker system, comprising:
   a first camera;
   a second camera; and
   a processor coupled to the first and second cameras, the processor comprising a first input for receiving a first image from the first camera, and a second input for receiving a second image from the second camera;
   wherein the processor is configured for determining one or more marker positions in the first image, determining one or more marker positions in the second image, and determining a position, an orientation, or both the position and the orientation, of the second camera using the one or more marker positions in the first image and the one or more marker positions in the second image;
   wherein the marker system comprises a plurality of markers, and the first and second cameras are oriented to view the plurality of markers.

24. The system of claim 23, wherein the marker system comprises a marker block having the plurality of markers.

25. The system of claim 23, wherein the marker system comprises one marker or a plurality of markers on a patient support, wherein the first and second cameras are oriented to view the one marker or the plurality of markers.

26. The system of claim 25, wherein the patient support comprises a positioner for placing the one marker or the plurality of markers to known positions.

27. The system of claim 23, further comprising a marker secured to a positioner, wherein the first and second cameras are oriented to view the marker.

28. The system of claim 23, wherein the processor is configured for determining the position, the orientation, or both the position and the orientation, of the second camera by:
   determining a first set of one or more rays associated with the first camera; and
   determining a second set of one or more rays associated with the second camera.

29. The system of claim 23, wherein the processor is configured for determining the position, the orientation, or both the position and the orientation, of the second camera by reducing or minimizing an epipolar error, a mismatch error, or both of the epipolar error and the mismatch error.

30. The system of claim 23, wherein the processor is configured for determining the position, the orientation, or both the position and the orientation, of the second camera by solving a set of equations, the set of equations derived using an epipolar error, a mismatch error, the position of the second camera, and the orientation of the second camera.

31. The system of claim 23, wherein the position or the orientation of the second camera is relative to the first camera.

32. The system of claim 23, wherein the position or the orientation of the second camera is relative to a treatment machine, a diagnostic machine, or a patient support.

33. A method of using a marker system, comprising:
   providing one or more markers; and
   obtaining a virtual marker system having a plurality of marker points, wherein the virtual marker system is obtained by moving the one or more markers from a first predetermined positions to a second predetermined position, and from the second predetermined position to a third predetermined position, wherein a number of the marker points is more than a number of the one or more markers.

34. The method of claim 33, further comprising using the plurality of marker points to determine a plane of a patient support.

35. The method of claim 34, wherein the plane is determined from the plurality of marker points using principal component analysis.

36. The method of claim 33, further comprising using the plurality of marker points to determine a plane in which the patient support moves.

37. The method of claim 36, wherein the plane is determined from the plurality of marker points using principal component analysis.

38. The method of claim 33, further comprising using the plurality of marker points to determine a focal length of a camera.

39. The method of claim 33, further comprising using the plurality of marker points to determine an aspect ratio associated with a camera.

* * * * *